United States Patent

Matsui et al.

[11] Patent Number: 5,536,852
[45] Date of Patent: Jul. 16, 1996

[54] PROCESS FOR THE PREPARATION OF TOCOPHEROL DERIVATIVES AND CATALYST

[75] Inventors: Makoto Matsui; Hisashi Yamamoto, both of Aichi Prefecture, Japan

[73] Assignee: Eisai Co., Ltd., Tokyo, Japan

[21] Appl. No.: 419,407

[22] Filed: Apr. 10, 1995

[30] Foreign Application Priority Data

Apr. 12, 1994 [JP] Japan .................................. 6-096994
Sep. 1, 1994 [JP] Japan .................................. 6-208358

[51] Int. Cl.⁶ .................................. C07D 311/72
[52] U.S. Cl. .................................. 549/411
[58] Field of Search .................................. 549/411

[56] References Cited

FOREIGN PATENT DOCUMENTS 50-89372  7/1975  Japan .

*Primary Examiner*—Patricia L. Morris
*Attorney, Agent, or Firm*—Wenderoth, Lind & Ponack

[57] ABSTRACT

A process is provided for the preparation of an α-tocopherol derivatives which are useful as antisterile vitamins, hypolipidemics, blood flow increasing agents, anti-cytosenility agents, antioxidants and the like. Catalysts are also provided.

The α-tocopherol derivatives are represented by the following formula (VII):

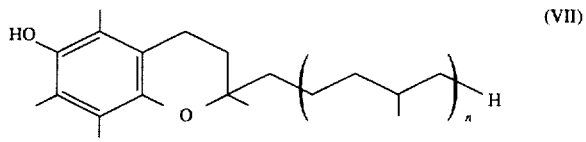

wherein n stands for 0 or an integer of from 1 to 5. The derivatives can be industrially prepared by employing as catalyst a metal ion-exchanged montmorillonite, metal ion-exchanged bentonite or metal ion-exchanged saponite which is substituted with one metal ion selected from the group consisting of scandium, yttrium, lanthanide element, aluminium, iron, tin, copper, titanium, zinc, nickel, gallium or zirconium.

9 Claims, No Drawings

PROCESS FOR THE PREPARATION OF TOCOPHEROL DERIVATIVES AND CATALYST

BACKGROUND OF THE INVENTION a) Field of the Invention

The present invention relates to a process for the preparation of α-tocopherol derivatives (VII) which are useful as antisterile vitamins, hypolipidemics, blood flow increasing agents, oxygen radical scavengers, anti-cytosenility agents, antioxidants and the like.

b) Description of the Related Art

α-Tocopherol derivatives represented by the following formula (VII):

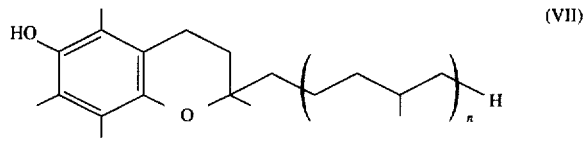

(VII)

wherein n stands for 0 or an integer of from 1 to 5 have heretofore each been prepared by condensing trimethylhydroquinone represented by the following formula (I):

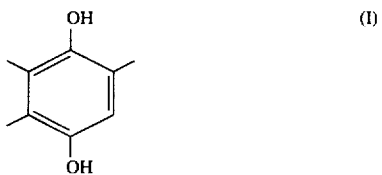

(I)

with one of phytols represented by the following formulae:

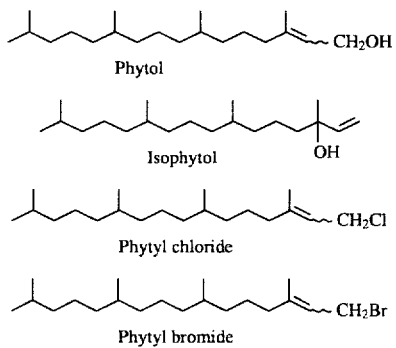

in accordance with a Friedel-Crafts reaction.

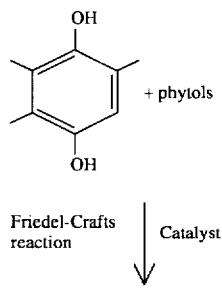

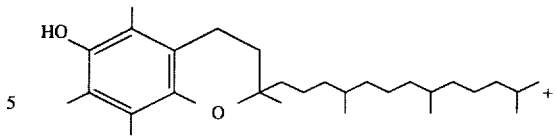

water

The catalyst is essential for the Friedel-Crafts reaction. Described specifically, Lewis acids such as zinc chloride, alumimum chloride, stannic chloride, ferric chloride, titanium tetrachloride and boron trifluoride-ether complex as well as combinations of Lewis acids and protonic acids such as hydrochloric acid, sulfuric acid and phosphoric acid have been used. However, these catalysts employed in the conventional preparation processes of α-tocopherol derivatives (VII) are accompanied by the problem that they cannot be recovered and reused because they are extremely unstable to water and are decomposed or deactivated upon contact with water formed in the reactions or during washing with water. Further, it is difficult from the standpoint of environmental conservation to dispose zinc, tin, phosphorus and the like. All of the conventional preparation processes are therefore not considered to be industrially suited.

In order to improve the aforementioned drawbacks, the utilization of fixed catalysts has been discussed. For example, Japanese Patent Publication No. 11709/81 discloses a process employing zeolite in which a substitutable group thereof is substituted with a proton, Japanese Patent Publication No. 22868/81 discloses a process employing silica-alumina, alumina-boria, zeolite and a fixed acid such as silica-alumina or alumina having zinc sulfate, nickel sulfate, aluminium sulfate or iron sulfate carried thereon, and Japanese Patent Publication No. 45195/85 discloses a process employing a metallic chelate sulfonic acid resins having a Lewis acid activity. Further, it has been known that a cation exchange resin is utilizable as the fixed catalyst.

In the case of the zeolite type catalyst described in Japanese Patent Publication No. 11709/81, such catalyst must be used preferably in an amount of 1–50 parts by weight to the feed material "trimethylhydroquinone (I)". This process was not an industrially actual process because the reaction volume is extremely increased. In addition, the obtained α-tocopherol had a GLC purity as low as 89–94% even when it was distilled under high vacuum, as described in Example.

The fixed acid carried on silica-alumina or alumina, described in Japanese Patent Publication No. 22868/81, involved problems, i.e. a larger amount of its use to the feed material and a yield as low as 20–65%. In order to improve the yield, furthermore, it was necessary to use an extremely toxic halogenated hydrocarbon such as perchloroethylene (tetrachloroethylene).

In the case of the metallic chelate sulfonic acid resin having a Lewis acid activity, described in Japanese Patent Publicattion No. 45195/85, the yield was 80–90% and this was not sufficient from the industrial standpoint.

Further, in the case of the cation exchange resin, it was not practical because of a very lower yield of 10%, as described in Comparative Example of Japanese Patent Publication No. 22868/81.

The conventional fixed catalysts employed in the preparation of the α-tocopherol derivatives (VII) involve many problems, for instance a lower yield and a need of a highly toxic solvent, as described above. It has therefore been desired to develop an industrially excellent fixed catalyst as a substitute for such conventional catalyst.

SUMMARY OF THE INVENTION

An object of the present invention is therefore to provide an industrially excellent process for the preparation of α-tocopherol derivatives (VII) which are useful as antisterile vitamins, hypolipidemics, blood flow increasing agents, oxygen radical scavengers, anti-cytosenility agents, antioxidants and the like.

The present inventors have therefore proceeded with extensive research to improve the above-described problems of the conventional fixed catalysts. As a result, it has been found that use of a particular metal ion-exchanged montmorillonite (IV), metal ion-exchanged bentonite (V) or metal ion-exchanged saponite (VI) can achieve the above object of industrial preparation of the α-Tocopherol (VII), and the present invention has been completed.

In one aspect of the present invention, there is thus provided a process for the preparation of an α-tocopherol derivative represented by the following formula (VII):

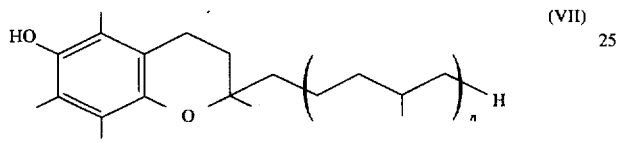

wherein n stands for 0 or an integer of from 1 to 5, which comprises subjecting trimethylhydroquinone represented by the following formula (I):

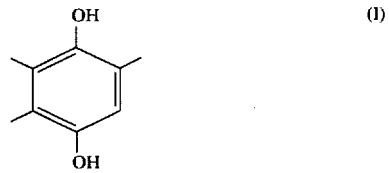

and an allyl alcohol derivative represented by the following formula (II):

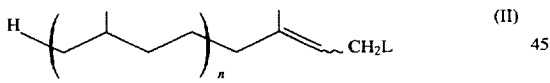

wherein n has the same meaning as defined above and L represents a hydroxy group or a halogen atom, acetoxy, methanesulfonyloxy, ethanesulfonyloxy, benzenesulfonyloxy or toluenesulfonyloxy group or an alkenyl alcohol represented by the following formula (III):

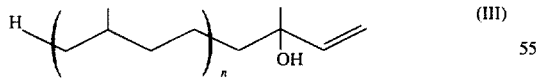

wherein n has the same meaning as defined above to a condensation reaction in the presence of a metal ion-exchanged montmorillonite (IV), metal ion-exchanged bentonite (V) or metal ion-exchanged saponite (VI).

Further in another aspect of the present invention, there is provided a catalyst mentioned below:

(1) scandium montmorillonite,
(2) scandium bentonite or
(3) scandium saponite.

DETAILED DESCRIPTION OF THE INVENTION AND PREFERRED EMBODIMENTS

Allyl alcohol derivatives employed in the present invention are represented by the following formula (II):

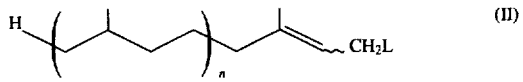

wherein n stands for 0 or an integer of from 1 to 5 and L represents a hydroxy group or a halogen atom, acetoxy, methanesulfonyloxy, ethanesulfonyloxy, benzenesulfonyloxy or toluenesulfonyloxy group. Specific examples of the halogen atom include chlorine, bromine, iodine and fluorine atoms.

Described specifically, examples of the allyl alcohol derivatives (II) in the present invention include, but are not limited to, the below-described compounds. Some of these compounds include those containing an asymmetric carbon atom in their molecules. Needless to say, all optically active substances thereof should be included, to say nothing of their racemic mixtures.

(1) Isoprenyl alcohol [also called "3-methyl-2-buten-1-ol"]
(2) Isoprenyl chloride [also called "1-chloro-3-methyl-2-butene"]
(3) Isoprenyl bromide [also called "1-bromo-3-methyl-2-butene"]
(4) Isoprenyl iodide [also called "1-iodo-3-methyl-2-butene"]
(5) 3,7-Dimethyl-2-octen-1-ol
(6) 1-Chloro-3,7-dimethyl-2-octene
(7) 1-Bromo-3,7-dimethyl-2-octene
(8) 1-Iodo-3,7-dimethyl-2-octene
(9) 3,7,11-Trimethyl-2-dodecen-1-ol
(10) 1-Chloro-3,7,11-trimethyl-2-dodecene
(11) 1-Bromo-3,7,11-trimethyl-2-dodecene
(12) 1-Iodo-3,7,11-trimethyl-2-dodecene
(13) Phytol
(14) Phytyl chloride
(15) Phytyl bromide
(16) Phytyl iodide
(17) Phytyl acetate
(18) Phytyl methanesulfonate
(19) Phytyl toluenesulfonate
(20) 3,7,11,15,19-Pentamethyl-2-icosen-1-ol
(21) 1-Chloro-3,7,11,15,19-pentamethyl-2-icosene
(22) 1-Bromo-3,7,11,15,19-pentamethyl-2-icosene
(23) 1-Iodo-3,7,11,15,19-pentamethyl-2-icosene
(24) 3,7,11,15,19,23-Hexamethyl-2-tetracosen-1-ol
(25) 1-Chloro-3,7,11,15,19,23-hexamethyl-2-tetracosene
(26) 1-Bromo-3,7,11,15,19,23-hexamethyl-2-tetracosene
(27) 1-Iodo-3,7,11,15,19,23-hexamethyl-2-tetracosene Next, alkenyl alcohols employed in the present invention are represented by the following general formula (III):

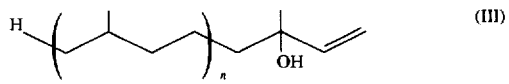

wherein n has the same meaning as defined above.

Described specifically, examples of the alkenyl alcohols (III) in the present invention include, but are not limited to, the below-described compounds. Some of these compounds include those containing an asymmetric carbon atom in their molecules. Needless to say, all optically active substances thereof should be included, to say nothing of their racemic mixtures.

(1) 2-Methyl-3-buten-2-ol
(2) 3,7-Dimethyl-1-octen-3-ol
(3) 3,7,11-Trimethyl-1-dodecen-3-ol
(4) Isophytol
(5) 3,7,11,15,19-Pentamethyl-1-icosen-3-ol
(6) 3,7,11,15,19,23-Hexamethyl-1-tetracosen-3-ol A metal ion-exchanged montomorillonite (IV), metal ion-exchanged bentonite (V) or metal ion-exchanged saponite (VI) employed in the present invention is montmorillonite (CAS Registration No. 1318-93-0), bentonite (CAB Registration No. 1302-78-9) or saponite $\{Na_x[Mg_3]\text{-}(Si_{4-x}Al_x)O_{10}(OH)_2\}$ as the constitutional component of clay, in which the metal ions ($Na^+$, $K^+$, $Mg^{2+}$, $Ca^{2+}$, $Al^{3+}$ and the like) thereof are substituted with one metal ion of elements selected from scandium, yttrium, lanthanide elements, aluminium, iron, tin, copper, titanium, zinc, nickel, gallium or zirconium. Although montomorillonite and bentonite are sometimes classified depending upon only the difference in product purity, their examples usable in the present invention include, but are not limited to, any products. Further, examples of montomorillonite, bentonite and saponite include, but are not limited to, natural and synthetic products, and all of them can be employed in the present invention.

The term "lanthanide element" used here means a lanthanum [La], cerium [Ce], praseodymium [Pr], neodymium [Nd], promethium [Pm], samarium [Sm], europium [Eu], gadolinium [Gd], terbium [Tb], dysprosium [Dy], holmium [Ho], erbium [Er], thullium [Tm], ytterbium [Yb] or lutetium [Lu] element.

The following compounds are specific examples of the metal ion-exchanged montmorillonite (IV), but are not limited to:

(1) scandium montmorillonite (hereinafter called "Sc-Mont")
(2) yttrium montmorillonite (hereinafter called "Y-Mont")
(3) aluminium montmorillonite (hereinafter called "Al-Mont")
(4) iron montmorillonite (hereinafter called "Fe-Mont")
(5) tin montmorillonite (hereinafter called "Sn-Mont")
(6) copper montmorillonite (hereinafter called "Cu-Mont")
(7) titanium montmorillonite (hereinafter called "Ti-Mont")
(8) zinc montmorillonite (hereinafter called "Zn-Mont")
(9) nickel montmorillonite (hereinafter called "Ni-Mont")
(10) gallium montmorillonite (hereinafter called "Ga-Mont")
(11) zirconium montmorillonite (hereinafter called "Zr-Mont")

Next, the following compounds are specific examples of the metal ion-exchanged bentonite (V), but are not limited to:

(1) Scandium bentonite (hereinafter called "Sc-Bent")
(2) Yttrium bentonite (hereinafter called "Y-Bent")
(3) Aluminium bentonite (hereinafter called "Al-Bent")
(4) Iron bentonite (hereinafter called "Fe-Bent")
(5) Tin bentonite (hereinafter called "Sn-Bent")
(6) Copper bentonite (hereinafter called "Cu-Bent")
(7) Titanium bentonite (hereinafter called "Ti-Bent")
(8) Zinc bentonite (hereinafter called "Zn-Bent")
(9) Nickel bentonite (hereinafter called "Ni-Bent")
(10) Gallium bentonite (hereinafter called "Ga-Bent")
(11) Zirconium bentonite (hereinafter called "Zr-Bent")

Further, the following compounds are specific examples of the metal ion-exchanged saponite (VI), but are not limited to:

(1) Scandium saponite (hereinafter called "Sc-Sap")
(2) Yttrium saponite (hereinafter called "Y-Sap")
(3) Aluminium saponite (hereinafter called "Al-Sap")
(4) Iron saponite (hereinafter called "Fe-Sap")
(5) Tin saponite (hereinafter called "Sn-Sap")
(6) Copper saponite (hereinafter called "Cu-Sap")
(7) Titanium saponite (hereinafter called "Ti-Sap")
(8) Zinc saponite (hereinafter called "Zn-Sap")
(9) Nickel saponite (hereinafter called "Ni-Sap")
(10) Gallium saponite (hereinafter called "Ga-Sap")
(11) Zirconium saponite (hereinafter called "Zr-Sap")

Sc-Mont, Sc-Bent and Sc-Sap according to the present invention are novel compounds and can be prepared in accordance with Preparation Examples hereinafter described. The metal ion-exchanged montmorillonites (IV), metal ion-exchanged bentonites (V) or metal ion-exchanged saponites (VI) other than the above-described novel compounds can be prepared in accordance with the processes described in Bulletin of Chemical Society of Japan, 60, 2689–2691, 1987 or the same bulletin, 61, 1237–1245, 1988 and the like. In addition, the feed materials, i.e. montmorillonite, bentonite and saponite, are readily available as reagents or industrial raw materials.

Finally, the α-tocopherol derivatives available according to the present invention are represented by the following general formula (VII):

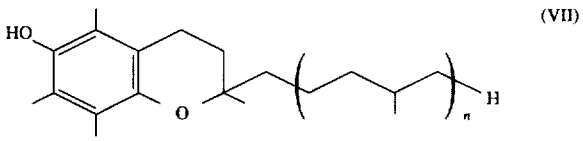

(VII)

wherein n has the same meaning as defined above.

Described specifically, examples of the a α-tocopherol derivatives (VII) in the present invention include, but are not limited to, the below-described compounds. Some of these compounds include those containing an asymmetric carbon atom in their molecules. Needless to say, all optically active substances thereof should be included, to say nothing of their racemic mixtures.

(1) 3,4-Dihydro-2,5,7,8-tetramethyl-2-methyl-2H-1-benzopyran-6-ol
(2) 3,4-Dihydro-2,5,7,8-tetramethyl-2-(4-methylpentyl)-2H-1-benzopyran-6-ol
(3) 3,4-Dihydro-2,5,7,8-tetramethyl-2-(4,8-dimethylnonyl)-2H-1-benzopyran-6-ol
(4) α-Tocopherol
(5) 3,4-Dihydro-2,5,7,8-tetramethyl-2-(4,8,12,16-tetramethylheptadecyl)-2H-1-benzopyran-6-ol
(6) 3,4-Dihydro-2,5,7,8-tetramethyl-2-(4,8,12,16,20-pentamethylhenicosyl)-2H-1-benzopyran-6-ol The preparation process according to the present invention will hereinafter be described in detail.

The preparation process can be conducted in a manner known per se in the art with respect to Friedel-Crafts reactions. In general, however, the trimethylhydroquinone (I) and the catalyst are mixed together, followed by adding a solvent if necessary. The resulting mixture is added with the allyl alcohol derivative (II) or the alkenyl alcohol (III) in an amount of about 0.9–1.1 equivalents relative to the trimethylhydroquinone (I). It is preferred to conduct the reaction under a stream of an inert gas such as nitrogen or argon and the like, although the reaction can be conducted without such an inert gas stream. The present invention is therefore not limited to the use of such an inert gas stream.

Where a solvent is employed, no particular limitation is imposed on the solvent in so far as it is inert to the trimethylhydroquinone (I), the allyl alcohol derivatives (II) or the alkenyl alcohol (III), and the catalyst. Specific examples include benzene, toluene, xylene, nitrobenzene, chlorobenzene, dichlorobenzene, nitromethane, tetrahydrofuran, 1,2-dimethoxyethane, ethyl ether, isopropyl ether, butyl ether, isobutyl ether, methyl acetate, ethyl acetate, propyl acetate, butyl acetate, methyl propionate, ethyl propionate, methyl butyrate, ethyl butyrate, methyl carbonate, ethyl carbonate, propyl carbonate, ethanol, propanol, butanol, pentanol, hexanol, cyclohexanol, acetone, butanone, pentanone, hexanone, cyclohexanone, methylisobutyl ketone, hexane, heptane, octane, decane, decalin, methylene chloride, chloroform, carbon tetrachloride, 1,2-dichloroethane, 1,1,1-trichloroethane, 1,1,2-trichloroethane, Tri-clene, 1,1,1,2-tetrachloroethane, 1,1,2,2-tetrachloroethane, 1-chloropropane, 2-chloropropane, 1,1-dichloropropane, 1,2-dichloropropane, 1,3-dichloropropane, 2,2-dichloropropane,1,4-dioxane and 1,3-dioxolane. Preferred are benzene, toluene, xylene, nitrobenzene, chlorobenzene, nitromethane, isobutyl ether, ethyl acetate, propyl acetate, methyl propionate, ethyl propionate, methyl butyrate, ethyl butyrate, pentanol, pentanone, hexanone, heptane, octane, methylene chloride, 1,2-dichloroethane, 1,1,1-trichloroethane, 1,1,2-trichloroethane and Tri-clene, with benzene, toluene, xylene, nitrobenzene, nitromethane, isobutyl ether, ethyl acetate, pentanol, pentanone, heptane, octane and methylene chloride being more preferred.

Although no particular limitation is imposed on the amount of the solvent to be used, the solvent may be employed usually in an amount of about 0.5~100 volumes, preferably in an amount of about 0.7~50 volumes, and more preferably in an amount of about 1~20 volumes, all relative to the trimethylhydroquinone (I). Incidentally, the above-exemplified solvents can be used either singly or in combination.

No particular limitation is imposed on the amount of the catalyst to be used in the present invention. The catalyst may be employed usually in an amount of about 1~200 wt %, preferably in an amount of about 10–100 wt %, and more preferably in an amount of about 20–60 wt %, all relative to the trimethylhydroquinone (I).

In the present invention, the catalyst can be recovered only by filtering the reaction liquid after completion of the reaction. The recovered catalyst can be reutilized, although its activation such as exchange of the metal ion never be carried out again. Further, the employed catalyst can be completely removed only by filtration, and hence any additional steps of water washing, disposal of waste liquid and the like are not needed. Therefore, the preparation process according to the present invention is considered to be extremely excellent from the economical and operational standpoints. In addition, no particular limitation is imposed on the kind of the reusable catalysts if they are the metal ion-exchanged montmorillonites (IV), metal ion-exchanged bentonites (V) or metal ion-exchanged saponites (VI) according to the present invention. Especially preferred are aluminium montmorillonite, aluminium bentonite and nickel saponite.

The reaction in the present invention can be conducted at room temperature to the reflux temperature of the solvent. Heating under reflux is generally preferred to shorten the reaction time. When heated under reflux, the reaction is generally completed in 30 minutes~12 hours or so. Further, the reaction time can be shortened further by azeotropically removing water.

The α-tocopherol derivatives (VII) so prepared can be purified by a method known per se in the art, such as chromatography on a silica gel column, HPLC or molecular distillation, and the like.

The preparation processes of Sc-Mont, Sc-Bent, Ga-Mont, Ni-Sap, Al-PM, Ni-Mont, Ti-Mont and Zr-Mont which are typical examples of catalyst employed in the practice of the present invention will be hereinafter described. The catalysts in the present invention are not limited to those catalysts alone.

PREPARATION PROCESSES

Preparation Example 1

Preparation of Scandium Bentonite (Sc-Bent)

Dissolved in 4 ml of distilled water were 500 mg (1.93 mmol) of scandium chloride hexahydrate, followed by adding 300 mg of bentonite (produced by Nakarai Tesch, Japan) at room temperature and stirring for 17 hours. After the reaction mixture was filtered under suction and the residue was washed with distilled water. The same residue was suspended in 6 ml of distilled water again and stirred for 3 hours. The resulting suspension was filtered under suction and the residue was washed with distilled water. This residue was then suspended in a mixed liquid consisting of 2 ml of distilled water and 2 ml of methanol, and the suspension was stirred for 2 hours. After the suspension was filtered under suction again and the residue was washed with distilled water, the same residue was collected and dried under reduced pressure at room temperature. The solidified clay-like solid was finely pulverized and dried again under reduced pressure at room temperature for 7 hours, whereby 204 mg of the title compound were obtained in the form of gray powders.

Preparation Example 2

Preparation of Scandium Montmorillonite (Sc-Mont)

Dissolved in 24 ml of distilled water were 3.113 g (12.0 mmol) of scandium chloride hexahydrate, followed by adding 3.0 g of sodium montmorillonite (produced by Kunimine Industry, Kunipia-F, Japan) at room temperature and stirring for 1.5 hours. After the reaction mixture was filtered under suction and the residue was washed with distilled water, the same residue was suspended in 24 ml of distilled water again and stirred for 1.5 hours. The resulting suspension was filtered under suction and the residue was washed with distilled water, and this residue was then suspended in a mixed liquid consisting of 12 ml of distilled water and 12 ml of methanol, and the suspension was stirred for 11 hours. After the suspension was filtered under suction again and the residue was washed with distilled water, the same residue was collected and dried under reduced pressure at room temperature. The solidified clay-like solid was finely pulverized and dried again under reduced pressure at room temperature for 16 hours, whereby 2.815 g of the title compound were obtained in the form of gray powders.

Preparation Example 3

Preparation of Gallium Montmorillonite (Ga-Mont)

Dissolved in 130 of distilled water were 25 g (62.5 mmol) of gallium nitrate [$Ga(NO_3)_3 \cdot nH_2O$, n=about 8], followed by adding 15.6 g of sodium montmorillonite (produced by Kunimine Industry, Kunipia-F, Japan) at room temperature and stirring for 16 hours. After the reaction mixture was filtered under suction and the residue was washed with distilled water, the same residue was suspended in 100 ml of distilled water again and stirred for 2 hours. The resulting suspension was filtered under suction and the residue was washed with distilled water, and this residue was then suspended in a mixed liquid consisting of 70 ml of distilled water and 70 ml of methanol, and the suspension was stirred for 2 hours. After the suspension was filtered under suction again and the residue was washed with distilled water, the same residue was collected and dried under reduced pressure at room temperature. The solidified clay was finely pulverized and dried again under reduced pressure at room temperature for 15 hours, whereby 15.5 g of the title compound were obtained in the form of gray powders.

Preparation Example 4

Preparation of Nickel Saponite (Ni-Sap)

Dissolved in 400 ml of distilled water were 58 g (200 mmol) of nickel nitrate [$Ni(NO_3)_2 \cdot 6H_2O$], followed by adding 50 g of sodium saponite (produced by Kunimine Industry, Sumekuton SA, Japan) at room temperature and stirring for 16 hours. After the reaction mixture was filtered under suction and the residue was washed with distilled water, the same residue was suspended in 400 ml of distilled water again and stirred for 2 hours. The resulting suspension was filtered under suction and the residue was washed with distilled water, and this residue was then collected and dried under reduced pressure at 100° C. for 2 hours. The solidified clay was finely pulverized, whereby 44.39 g of the title compound were obtained in the form of gray powders.

Preparation Example 5

Preparation of Calcined Nickel Saponite

The clay obtained in Preparation Example 4 was sintered at 400° C. for 4 hours, whereby 2.207 g of the title compound were obtained in the form of gray powders.

Preparation Example 6

Preparation of Aluminium-Bridged Montmorillonite (Al-PM)

Dissolved in 100 ml of distilled water were 7.5 g (20 mmol) of aluminium nitrate [$Al(NO_3)_3 \cdot 9H_2O$], followed by adding dropwise 80 ml of a 0.5N aqueous solution of sodium hydroxide at 60° C. over 80 minutes. The resulting solution was stirred at the same temperature for 2 hours as it was, and further stirred at room temperature for 1 hour. To the same solution was then added 2.4 g of sodium montmorillonite and stirred overnight. After the reaction mixture was filtered under suction and the residue was washed with distilled water, this residue was collected and dried under reduced pressure at 100° C. for 5 hours. The solidified clay was finely pulverized, whereby 2.43 g of the title compound were obtained in the form of gray powders.

Preparation Example 7

Preparation of Calcined Aluminium-Bridged Montmorillonite

The clay obtained in Preparation Example 6 was sintered at 400° C. for 4 hours, whereby 1.28 g of the title compound were obtained in the form of gray powders.

Preparation Example 8

Preparation of 1N-Hydrochloric Acid-Treated Nickel Montmorillonite (Ni-Mont)

Dissolved in 800 ml of distilled water were 116 g (400 mmol) of nickel nitrate, followed by adding 100 g of sodium montmorillonite at room temperature and stirring for 13 hours. After the reaction mixture was filtered under suction and the residue was washed with distilled water, the same residue was suspended in 400 ml of distilled water again and stirred for 1.3 hours. The resulting suspension was filtered under suction and the residue was washed with distilled water, and this residue was then suspended in a mixed liquid consisting of 200 ml of distilled water and 200 ml of methanol, and the suspension was stirred for 1.3 hours. After the suspension was filtered under suction again and the residue was washed with distilled water, the same residue was collected and dried under reduced pressure at 100° C. for 4 hours. The solidified clay was finely pulverized and dried under reduced pressure at 50°–90° C. for 2 hours. Five g of a part of the produced clay were suspended in 30 ml of 1N-hydrochloric acid and stirred at room temperature for 2 hours. After the resulting suspension was filtered and the reidue was dried at 100° C. for 10 hours, this residue was finely pulverized, whereby 4.41 g of the title compound were obtained in the form of gray powders.

Preparation Example 9

Preparation of 5N-Hydrochloric Acid-Treated Nickel Montmorillonite (Ni-Mont)

Dissolved in 800 ml of distilled water were 116 g (400 mmol) of nickel nitrate, followed by adding 100 g of sodium montmorillonite at room temperature and stirring for 13 hours. After the reaction mixture was filtered under suction and the residue was washed with distilled water, the same residue was suspended in 400 ml of distilled water again and stirred for 1.3 hours. The resulting suspension was filtered under suction and the residue was washed with distilled water, and this residue was then suspended in a mixed liquid consisting of 200 ml of distilled water and 200 ml of methanol, and the suspension stirred for 1.3 hours. After the suspension was filtered under suction again and the residue was washed with distilled water, the same residue was collected and dried under reduced pressure at 100° C. for 4 hours. The solidified clay was finely pulverized and dried under reduced pressure at 50°–90° C. for 2 hours. Five g of a part of the produced clay were suspended in 50 ml of 5N-hydrochloric acid and stirred at room temperature for 2 hours. After the resulting suspension was filtered and the reidue was dried at 100° C. for 10 hours, this residue was finely pulverized, whereby 3.95 g of the title compound were obtained in the form of gray powders.

Preparation Example 10

Preparation of Titanium Montmorillonite (Ti-Mont)

A hydrochloric acid solution was previously prepared from 400 ml of 1N-hydrochloric acid and 20 ml of concentrated hydrochloric acid. To the hydrochloric acid solution were dissolved 56.8 g (199 mmol) of titaniun isopropoxide [Ti(O-iPr)$_4$], followed by adding 50 g of sodium montmorillonite at room temperature and stirring for 2.5 hours. After the reaction mixture was filtered under suction and the residue was washed with distilled water, the same residue was suspended in 400 ml of distilled water again and stirred for 14 hours. The resulting suspension was filtered under suction and the residue was washed with distilled water, and this residue was then suspended in 200 ml of distilled water and stirred for 2 hours. After this suspension procedure and filteration procedure was repeated five times, the residue was washed with distilled water and this residue was collected and dried under reduced pressure at 100° C. for 6 hours. The solidified clay was finely pulverized and dried again under reduced pressure at 100° C. for 4 hours, whereby 54.1 g of the title compound were obtained in the form of gray powders.

Preparation Example 11

Preparation of Zirconium Montmorillonite (Zr-Mont)

Dissolved in 200 ml of distilled water were 24 g (103 mmol) of zirconium tetrachloride (ZrCl$_4$), followed by adding 25.8 g of sodium montmorillonite at room temperature and stirring for 18 hours. After the reaction mixture was filtered under suction and the residue was washed with distilled water, the same residue was suspended in 200 ml of distilled water again and stirred for 1.5 hours. After this suspension procedure and filteration procedure was repeated four times, the residue was washed with distilled water and this residue was collected and dried under reduced pressure at 100° C. for 6 hours. The solidified clay was finely pulverized and dried again under reduced pressure at 90° C. for 2 hours, whereby 23.422 g of the title compound were obtained in the form of gray powders.

Finally, Examples will be described hereinafter to practically substantiate the present invention. Needless to say, it should be borne in mind that the present invention is not limited to the Examples.

Example 1

Synthesis of α-Tocopherol

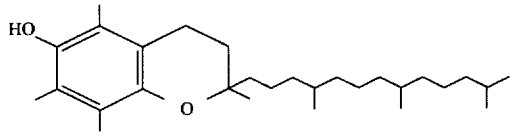

Suspended in 1 ml of toluene were 200 mg (1.316 mmol) of trimethylhydroquinone (TMH) and 100 mg of Sc-Bent, followed by heating under reflux for 10 minutes under an argon gas stream. After a solution of 430 mg (1.45 mmol) of isophytol in 1 ml of toluene was added dropwise over 5 minutes under heating and reflux, TMH and isophytol were further reacted each other for 1 hour. The reaction liquid was cooled, to which 20 ml of n-hexane were added. The resulting mixture was filtered and then concentrated under reduced pressure. The residue was purified by chromatography on a silica gel column (eluent: n-hexane-ether system), whereby 527 mg of the title compound were obtained in the form of a brown oil. (Yield: 93%, GLC purity: 99%)

The product was identified with a standard reference material (SRM) in TLC, HPLC, capillary GLC, $^1$H-NMR spectrum, IR spectrum and mass spectrum.

Examples 2–14

Synthesis of α-Tocopherol

The following results were obtained in the same manner as described in the preceding Example 1.

TABLE 1

| Example | Catalyst | Amount of catalyst | TMH (mg) | Isophytol (mg) | Reaction solvent | Reaction conditions | Yield (%) | Purity (%) |
|---|---|---|---|---|---|---|---|---|
| 2 | So-Mont | 100 mg | 200 mg | 430 mg | Toluene 1 ml | Heated under reflux, 3 hrs | 80 | 99.3 |
| 3 | Al-Mont | " | " | " | " | Heated under reflux, 3 hrs | 95 | 98.0 |
| 4 | Fe-Mont | 500 mg | 1000 mg | 2029 mg | Toluene 2 ml | Heated under reflux, 3 hrs | 92 | 99.4 |
| 5 | Zn-Mont | 200 mg | 200 mg | 430 mg | Toluene 1 ml | Heated under reflux, 3 hrs | 94 | 99.5 |
| 6 | Al-Mont | 500 mg | 1000 mg | 2029 mg | Toluene 2 ml | Heated under reflux, 3 hrs | 94 | 98.0 |
| 7 | Sn-Mont | " | " | " | " | Heated under reflux, 3 hrs | 98 | 97.6 |
| 8 | Ga-Mont | " | " | " | " | Heated under reflux, 3 hrs | 97 | 97.1 |
| 9 | Gu-Mont | " | " | " | " | Heated under reflux, 2.5 hrs | 98 | 100 |
| 10 | Ni-Mont | " | " | " | " | Heated under reflux, 3 hrs | 97 | 99.6 |
| 11 | Ni-Sap | " | " | " | " | Heated under reflux, 3 hrs | 90 | 87.8 |
| 12 | Ni-Sap* | " | " | " | " | Heated under reflux, 3 hrs | 93 | 88.0 |
| 13 | Al-PM | " | " | " | " | Heated under | 100 | 97.2 |

TABLE 1-continued

| Example | Catalyst | Amount of catalyst | TMH (mg) | Isophytol (mg) | Reaction solvent | Reaction conditions | Yield (%) | Purity (%) |
|---|---|---|---|---|---|---|---|---|
| 14 | Al-PM* | " | " | " | " | reflux, 3 hrs Heated under reflux, 3 hrs | 98 | 95.7 |

Purity: GLC pwity in all
Catalyst*: Sintered catalyst

Example 15

Synthesis of α-Tocopherol

Suspended in 75 ml of octane were 24.9 g (0.164 mol) of TMH and 12.5 g of Ti-Mont, followed by heating under reflux for 20 minutes under an argon gas stream. After 46.2 g (0.153 mol) of isophytol were added dropwise over 3 hours under heating and reflux, THM and isophtol were reacted for additional 2 hour. The reaction liquid was cooled, to which 150 ml of ether were added. The resulting mixture was filtered, and then washed with water (150 ml×2), 1N-sodium hydroxide (150 ml×1) and water (150 ml×3), followed by drying it over magnesium sulfate. The dried matter was concentrated under reduced pressure, whereby 65.6 g of the title compound were obtained in the form of a brown oil. (Yield: 100%, GLC purity: 94.1%)

Examples 16–25

Synthesis of α-Tocopherol

The following results were obtained by changing the solvent in the same manner as described in Example 1.

TABLE 2

| Example | Catalyst | Amount of catalyst | TMH (mg) | Isophytol (mg) | Reaction solvent | | Reaction conditions | Yield (%) | Purity* (%) |
|---|---|---|---|---|---|---|---|---|---|
| 16 | Al-Mont | 500 mg | 1000 mg | 2029 mg | Heptane | 2 ml | | 88% | 98.4%* |
| 17 | " | " | " | " | Octane | 2 ml | | 98% | 97.6%* |
| 18 | " | " | " | " | 1-Pentanol | 2 ml | | 94% | 93.5%* |
| 19 | " | " | " | " | 3-Pentanon | 2 ml | | 94% | 98.8%* |
| 20 | " | " | " | " | Butyl acetate | 2 ml | Heated | 93% | 92.5%* |
| 21 | " | " | " | " | Isobutyl ether | 2 ml | under | 98% | 99.0%* |
| 22 | Ni-Mont | " | " | " | Toluene | 2 ml | reflux, | 100% | 91.4%** |
| 23 | " | " | " | " | Xylene | 2 ml | 3 hours | 96% | 91.2%** |
| 24 | " | " | " | " | Octane | 2 ml | in all | 92% | 95.4%** |
| 25 | " | " | " | " | Methylisobutyl ketone +Octane | 2 ml | | 91% | 95.4%** |

Purity: *GLC purity, **HPLC purity

Examples 26–29

Synthesis of α-Tocopherol

The following results were obtained by repeatedly reutilizing four times the Al-Mont recovered in Example 6.

TABLE 3

| Example | Catalyst | Amount of catalyst | TMH (mg) | Isophytol (mg) | Reaction solvent | Reaction conditions | Yield (%) | Purity (%) |
|---|---|---|---|---|---|---|---|---|
| 6 | Al-Mont | 500 mg | 1000 mg | 2029 mg | Toluene 2 ml | Heated under reflux, 3 hrs | 94% | 98% |
| 26 | Reused 1 | 100 mg | 200 mg | 430 mg | Toluene 1 ml | Heated under reflux, 3 hrs | 97% | 98% |
| 27 | Reused 2 | " | " | " | " | Heated under reflux, 3 hrs | 89% | 96% |
| 28 | Reused 3 | " | " | " | " | Heated under reflux, 3 hrs | 87% | 94% |
| 29 | Reused 4 | " | " | " | " | Heated under reflux, 3 hrs | 72% | 94% |

Purity: HPLC purity in all

Examples 30–33

Synthesis of α-Tocopherol

The following results were obtained by repeatedly reutilizing four times the recovered Ni-Mont.

TABLE 4

| Example | Catalyst | Amount of catalyst | TMH (mg) | Isophytol (2 g) | Reaction solvent | Reaction conditions | Yield (%) | Purity (%) |
|---|---|---|---|---|---|---|---|---|
|  | Ni-Mont | 500 mg | 1000 mg | 2029 mg | Toluene 2 ml | Heated under reflux, 3 hrs | 100% | 98.5% |
| 30 | Reused 1 | 416 mg | 830 mg | 1680 mg | Toluene 2ml | Heated under reflux, 3 hrs | 100% | 98.1% |
| 31 | Reused 2 | 400 mg | 800 mg | 1620 mg | " | Heated under reflux, 3 hrs | 100% | 97.9% |
| 32 | Reused 3 | 344 mg | 688 mg | 1390 mg | " | Heated under reflux, 3 hrs | 100% | 97.9% |
| 33 | Reused 4 | 377 mg | 674 mg | 1370 mg | " | Heated under reflux, 3 hrs | 100% | 98.2% |

Purity: GLC purity in all

What is claimed is:

1. A process for the preparation of an α-tocopherol derivative represented by the following formula (VII):

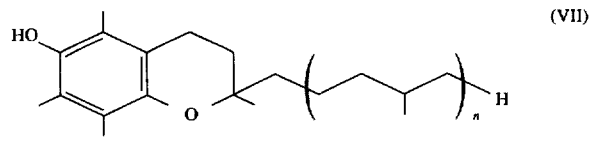

wherein n stands for 0 or an integer of from 1 to 5, which comprises subjecting trimethylhydroquinone represented by the following formula (I):

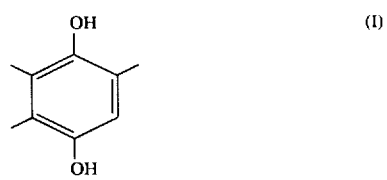

and an allyl alcohol derivative represented by the following formula (II):

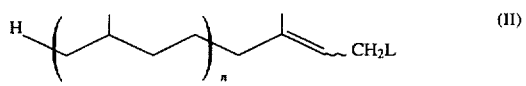

wherein n has the same meaning as defined above and L represents a hydroxyl group or a halogen atom, acetoxy, methanesulfonyloxy, ethanesulfonyloxy, benzenesulfonyloxy or toluenesulfonyloxy group, or an alkenyl alcohol represented by the following formula (III):

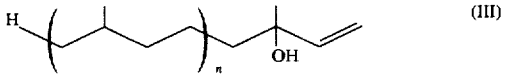

wherein n has the same meaning as defined above to a condensation reaction in the presence of a metal ion-exchanged montmorillonite (IV), metal ion-exchanged bentonite (V) or metal ion-exchanged saponite (VI).

2. A process for the preparation of an α-tocopherol derivative (VII), according to claim 1, wherein the metal is one selected from the group consisting of scandium, yttrium, lanthanide element, aluminium, iron, tin, copper, titanium, zinc, nickel, gallium or zirconium, wherein the lanthanide element means lanthanum, cerium, praseodymium, neodymium, promethium, samarium, europium, gadolinium, terbium, dysprosium, holmium, erbium, thulium, ytterbium or lutetium.

3. A process for the preparation of an α-tocopherol derivative (VII), according to claim 1, wherein one or more solvents selected from a group consisting of benzene, toluene, xylene, nitrobenzene, nitromethane, isobutyl ether, ethyl acetate, pentanol, pentanone, heptane, octane and methylene chloride are used as a solvent.

4. A process for the preparation of an α-tocopherol derivative (VII), according to claim 1 wherein the metal ion-exchanged montmorillonite (IV), metal ion-exchanged bentonite (V) or metal ion-exchanged saponite (VI) is recovered and reused.

5. A process for the preparation of an α-tocopherol derivative (VII), according to claim 4, wherein the metal is aluminium or nickel.

6. A process for the preparation of an α-tocopherol derivative (VII), according to claim 2, wherein one or more solvents selected from a group consisting of benzene, toluene, xylene, nitrobenzene, nitromethane, isobutyl ether, ethyl acetate, pentanol, pentanone, heptane, octane and methylene chloride are used as a solvent.

7. A process for the preparation of an α-tocopherol derivative (VII), according to claim 2, wherein the metal ion-exchanged montmorillonite (IV), metal ion-exchanged bentonite (V) or metal ion-exchanged saponite (VI) is recovered and reused.

8. A process for the preparation of an α-tocopherol derivative (VII), according to claim 3, wherein the metal ion-exchanged montmorillonite (IV), metal ion-exchanged bentonite (V) or metal ion-exchanged saponite (VI) is recovered and reused.

9. A process for the preparation of an α-tocopherol derivative (VII), according to claim 7, wherein the metal ion-exchanged montmorillonite (IV), metal ion-exchanged bentonite (V) or metal ion-exchanged saponite (VI) is recovered and reused.

* * * * *